(12) United States Patent
Murray

(10) Patent No.: US 7,997,294 B2
(45) Date of Patent: Aug. 16, 2011

(54) SOIL MOISTURE SENSING APPARATUS FOR PREVENTING OVERWATERING

(76) Inventor: Donald Murray, Oakland, CA (US)

(*) Notice: Subject to any disclaimer, the term of this patent is extended or adjusted under 35 U.S.C. 154(b) by 319 days.

(21) Appl. No.: 12/182,921

(22) Filed: Jul. 30, 2008

(65) Prior Publication Data

US 2010/0024295 A1 Feb. 4, 2010

(51) Int. Cl.
*F16K 17/36* (2006.01)
(52) U.S. Cl. .................. 137/78.3; 73/73; 239/63
(58) Field of Classification Search ............ 137/73.2, 137/73.3, 363, 544, 550, 78.2, 78.3; 73/73, 73/306, 319; 340/624; 239/63, 65
See application file for complete search history.

(56) References Cited

U.S. PATENT DOCUMENTS

| | | | |
|---|---|---|---|
| 3,261,125 A * | 7/1966 | Arkebauer | 47/81 |
| 3,374,324 A * | 3/1968 | McGrann | 200/84 B |
| 3,553,481 A | 1/1971 | Hasenbeck | |
| 3,945,247 A * | 3/1976 | Anderson | 73/73 |
| 4,014,359 A | 3/1977 | Sanner | |
| 4,352,735 A * | 10/1982 | Turetsky | 210/238 |
| RE31,204 E | 4/1983 | Sanner | |
| 4,513,608 A | 4/1985 | Cuming | |
| 4,531,087 A * | 7/1985 | Larson | 324/696 |
| 4,541,446 A * | 9/1985 | Hogan | 137/2 |
| 4,662,563 A | 5/1987 | Wolfe, Jr. | |
| 4,684,920 A | 8/1987 | Reiter | |
| 4,693,419 A | 9/1987 | Weintraub et al. | |
| 4,726,143 A * | 2/1988 | Steinbeck | 47/48.5 |
| 4,876,647 A | 10/1989 | Gardner et al. | |
| 4,884,436 A * | 12/1989 | Ankeny et al. | 73/38 |
| 4,922,433 A | 5/1990 | Mark | |
| 5,207,380 A | 5/1993 | Harryman | |
| 5,241,978 A * | 9/1993 | Shaw et al. | 137/78.2 |
| 5,279,071 A | 1/1994 | McDougall | |
| 5,329,081 A | 7/1994 | Jones | |
| 5,348,227 A | 9/1994 | Polonsky | |
| 5,400,815 A | 3/1995 | Whitehill | |
| 5,853,125 A * | 12/1998 | Murray | 239/63 |
| 6,378,779 B1 * | 4/2002 | Taylor | 239/63 |

(Continued)

FOREIGN PATENT DOCUMENTS

WO WO 87/00725 2/1987

(Continued)

OTHER PUBLICATIONS

Banks, J. "Irrigation for Home Gardens"; Mar. 3, 2006; Presented at the Western Regional Leaders Forum Workshop "Irrigating Home Gardens the Easy and Efficient Way"; USU Extension Agency; http://www.sydneywaer.com.au/SavingWater/InYourGarden/WateringSystems.

(Continued)

*Primary Examiner* — Stephen M Hepperle
*Assistant Examiner* — Kevin Murphy
(74) *Attorney, Agent, or Firm* — Michael A. Glenn; Glenn Patent Group

(57) ABSTRACT

A soil moisture sensing system includes a housing embedded in the soil and having a water chamber adapted to receive water from a water source. A controlled drainage assembly includes a semi-permeable membrane coupled to said water chamber for controllably releasing water from the water chamber. A magnetically actuated switch is coupled to a float in the water chamber to provide a control signal when the water level in the water chamber is at a predetermined level.

9 Claims, 1 Drawing Sheet

U.S. PATENT DOCUMENTS

| | | | |
|---|---|---|---|
| 6,460,563 | B2 | 10/2002 | Olson et al. |
| 6,802,932 | B2 | 10/2004 | Kudo et al. |
| 6,834,662 | B1 | 12/2004 | Olson et al. |
| 7,222,454 | B1 | 5/2007 | Chen |
| 2001/0045230 | A1 | 11/2001 | Olson et al. |
| 2007/0267515 | A1 | 11/2007 | Sargent |

FOREIGN PATENT DOCUMENTS

| | | |
|---|---|---|
| WO | WO 02/099543 | 12/2002 |
| WO | WO 2004/014127 | 2/2004 |
| WO | WO 2006/068900 | 6/2006 |
| WO | WO 2006/068919 | 6/2006 |
| WO | WO 2007/136531 | 11/2007 |

OTHER PUBLICATIONS

Bremer, D.: "Soil-moisture sensors can help regulate irrigation"; Jun. 1, 2003; TurfGrass/Trends; http://www.turfgrasstrends.com/turfgrasstrends/article/articleDetail.jsp?if-58294.

"Closed-loop Irrigation"; retrieved Apr. 25, 2008; http://www.acclima.com/Solutions/closedloop.htm.

"Efficient irrigation"; retrieved Apr. 25, 2008; http://www.greenbuilder.com/sourcebook/XeriscapeGuideline5.html.

Fleitner, M.; "Smart watering systems"; copyright 2006; retrieved Apr. 25, 2008; BobVila.com; http://ww.bobvila.com/HowTo_Lirbrary/Smart_Watering_Systems-Irrigation-A1970.html.

"IL200-MC Irrigation Moisture Clik™"; Apr. 25, 2008; http://www.dynamax.com/ii200-mc.htm.

"Inground irrigation systems"; undated; The City of Calgary; www.irrigation.org/certification.

"Irritrol systems: controllers"; copyright Toro Australia Pty Limited 2006; retrieved on Apr. 25, 2008; http://www.toro.com.au/irrigation/irritrol_category.cfm?cat=8.

Jesson, C.; "Irrigation: Irrigation regulation"; Jan. 2007; http://www.totallandscapecare.net/apps/news/articletic.asp?id=57355.

McGuirk, S.; "Irrigation sensors for the landscape"; retrieved on Apr. 25, 2008; 4http://grounds-mag.co/mag/grounds_maintenance_irrigaiton_sensors_landscape_2/index.htm.

Mecham, T.; *WaterWatcher, Inc. is pleased to introduce the WaterWatcher DPS—100 system for use with residential and light commercial irrigation systems*; Mar. 7, 2003; WaterWater, Inc; http://www.prweb.com/releases/2003/3/prweb59366.htm.

Peak, C.; "Soil moisture monitoring in landscape irrigation and water re-use"; Dec. 1996; http://www.peakmonitoring.com.au/fileds/Download/IAA%20article%20Sept%2006.pdf.

Powell, A. "Lawn irrigation with automatic systems"; Oct. 1996; http;//www.ca.uky.edu/agc/pubs/agr/agr115/agr115.htm.

"Rain bird—the intelligent use of water"; copyright 1996-2008, Rain Bird Corporation; Application Guide: Over-watering (weather); www.rainbird.com/iuow/appguide_over_weather.html.

Ryan, H., et al.; "Irrigation systems and trees"; Jul. 2002; Dept. of Natural Resources Conservation, Univ. of Massachusetts, Amherst.

"Soil moisture monitoring in landscape irrigation & water re-use"; retrieved on Apr. 25, 2008; Sentek Sensor Technologies—Soil moisture monitoring specialists; http://www.sentek.com.au/new/whatsnew.asp?lang=en&id=1064.

*Why Acclima irrigation works*; Efficient irrigation-Smart Irrigation; 2008 Efficient Irrigation Resources; http://www.efficientirrigation.com/08resources/whi-it-works.htm; updated Mar. 24, 2008.

"WiSA up and get the best out of every drop"; retrieved on Apr. 25, 2008; WiSA Irrigation Solutions: http;//www.irrigatewise.co.au/.

Ya'akobi, J.; "Garden irrigation—what does over-watering really mean?"; Apr. 16, 2008; Enzine Articles; 4http://ezinearticles.com/?Garden-Irrigation-What-Does-Over-Watering-Really-Mean?&ids=1113609.

Southwest Florida Water Management District; "Saving water outdoors: Irrigation"; retrieved on Apr. 25, 2008; http://www.swfwmd.state.fl.us/conservation/outdoors/irrigation.php.

\* cited by examiner though the grate 118 overlies the basin 104 and has a number of through holes formed therein for admitting water into the basin 104. A circular porous filter member 120 is formed from a sheet of filter fabric material, which is typically used to cover French drains, helps to prevent dirt or debris from passing into and through the basin portion 110 from the ground level.

SOIL MOISTURE SENSING APPARATUS FOR PREVENTING OVERWATERING

BACKGROUND OF THE INVENTION

1. Technical Field

This invention relates to apparatus and systems for sensing soil moisture and for preventing overwatering.

2. Description of the Prior Art

Overwatering of plants can occur either intentionally or unintentionally. The actual need for watering is dependent upon the moisture content of the soil in which plants are rooted. Too much moisture can be harmful to plants. Watering systems, such as sprinkler systems, drip systems, and irrigation systems, are often have automatic timers and have no means for determining the actual moisture content of the soil. These automatic systems can therefore operate without regard to the actual moisture condition of the soil or the needs of the plants. The soil can be saturated when a timer calls for more water from a source. For example, plants can be overwatered by automatic watering systems during times of heavy rainfall, when the soil may actually be saturated. An overzealous grower or gardener can also unintentionally overwater plants. Beside water sources that deliver water to the soil surface from, for example, sprinkler systems, drip systems, and irrigation systems, other unintentional water sources can be ground water that seeps into the soil surrounding plants to the plants below grade and in effect raises the local water table to perhaps saturate the soil around the plants. This can occur due to seasonal or intermittent springs as well as subterranean seepage or runoff, whether intentional or unintentional, from adjacent property. In some of these situation, the grower or gardener is often not aware of the soil moisture accidentally being excessive. Overwatering can also result in excessive runoff from a water saturated property onto sidewalks, streets, gutters, which wastes water and is a nuisance.

Consequently, a need exists for a system that can sense soil moisture and provide a signal indicating that the soil is currently saturated and not in need of water.

SUMMARY OF THE INVENTION

The present invention provides soil moisture sensing apparatus that includes a housing embedded in the soil and having a water chamber that is adapted to receive water from a water source. Means are coupled to the lower end of the housing for controllably releasing water from the water chamber. Water level sensing means are provided for sensing a predetermined water level in the water chamber where such means includes a semi-permeable membrane that controllably releases water from the water chamber. The means coupled to the lower end of the housing for controllably releasing water from the water chamber includes an assembly contained with a cap that includes a first porous filter; a first spacer ring located above the first filter; a semi-permeable membrane located above the first spacer ring; a second spacer ring located above the semi-permeable membrane; a second porous filter located above the second spacer ring; and wherein the first and second filters are spaced apart from the semi-permeable membrane by the spacer rings. The water level sensor include a float that magnetically actuates a switch that provide a control signal. A porous filter is located within the upper basin and a grate covers the upper basin.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

Figure 1:
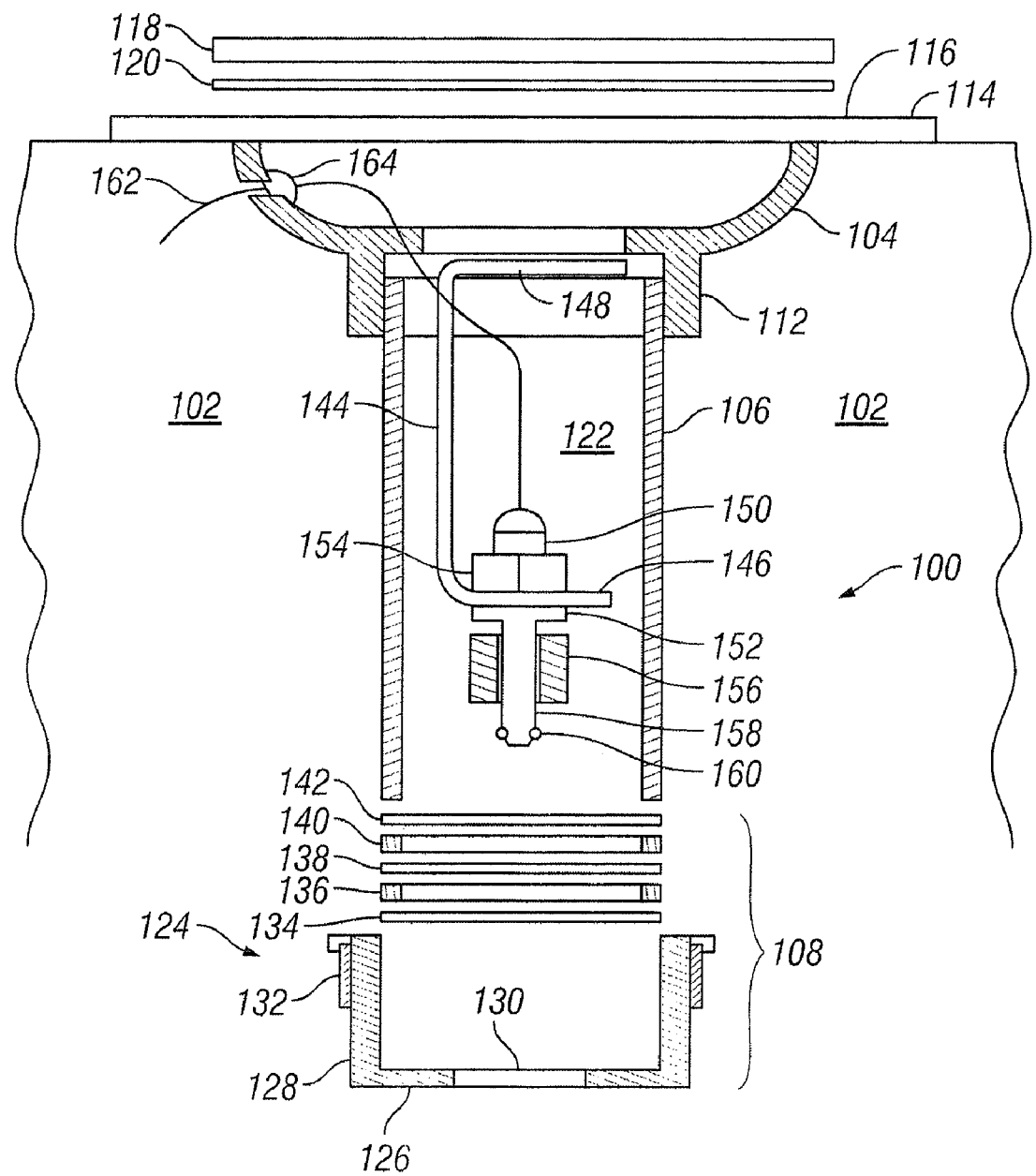
FIG. 1 is a side, partly sectional, partly exploded view of a soil moisture sensing apparatus for preventing excessive overwatering according to the present invention.

Reference is now made in detail to a preferred embodiments of the invention, an example of which is illustrated in the accompanying drawing. While the invention is described in conjunction with the preferred embodiment, it will be understood that it is not intended to limit the invention to these embodiments. On the contrary, the invention is intended to cover alternatives, modifications and equivalents, which may be included within the spirit and scope of the invention as defined by the appended claims.

FIG. 1 illustrates an embodiment of a soil moisture sensing apparatus 100 that is embedded in the soil 102 for preventing overwatering of the soil 102 around the apparatus.

A housing for the apparatus 100 includes an upper basin 104 that is formed, for example, of a polyvinyl chloride (PVC) material and that is connected to the upper end of a cylindrical pipe 106 that is formed, for example, of an acrylonitride butadiene styrene (ABS) material. A lower endcap assembly 108 is connected to the lower end of the pipe 106.

In use, the soil moisture sensing apparatus 100 is partially embedded in the soil 102 and is positioned vertically in the soil so that the upper basin 104 portion is near the surface of the soil to collect water at or above ground. The cylindrical pipe 106 extends downwardly into the soil with the lower endcap assembly 108 at the lower end of the moisture sensing apparatus.

The basin 104 has a curved basin portion from which downwardly extends an annular lower flange 112. The upper end of the cylindrical pipe 106 fits into and is secured to the annular lower flange 112 with a suitable adhesive. A laterally extending square flange 114 extends from the top of the basin 104 102. In use, the square flange 114 is located at or near the surface of the soil. A circular recessed groove 116 formed in the flange 114 of the upper basin 104 provides support for the peripheral margins of a circular grate, or cover, 118. The grate 118 overlies the basis 104 and has a number of through holes formed therein for admitting water into the basin 104. A circular porous filter member 120 is formed from a sheet of filter fabric material, which is typically used to cover French drains, helps to prevent dirt or debris from passing into and through the basin portion 110 from the ground level.

The interior of the cylindrical pipe 106 serves as a water chamber 122 that receives water from the upper surface of the soil. Note as described herein below that the water chamber 122 under certain conditions of saturated soil can also receive water from below ground level.

The lower endcap assembly 108 in this embodiment is removably attached to the lower end of the pipe 106. The lower endcap assembly 108 provides means for controllably releasing water from the water chamber 122. The lower endcap assembly 108 includes a cap member 124 that has a circular base plate 126 and a cylindrical peripheral flange 128 that extends from the peripheral margins of the base plate 126. An aperture 130 is formed through the base plate 126 of the cap member 124 to permit water to flow out of the endcap assembly 108. The lower end of the cylindrical pipe 106 fits within the cylindrical peripheral flange 128 of the cap member 124. The cap member 124 is formed of a flexible material and is held in position on the cylindrical pipe 106 with a hose clamp 132 which extends circumferentially around the peripheral flange 128 of the cap member 124.

The cylindrical peripheral flange cap member 124 holds the other components of the lower endcap assembly 108 in place. Contained within the cap member 124 is a first circular porous filter 134 that is formed as a thin disk of filter fabric material and that is located adjacent the base plate 126 of the cap member 124 to cover aperture 130 and helps to prevent dirt or debris from the aperture 130 from passing into the lower endcap assembly 108. A first spacer ring ABS material is located above the first porous filter 134. A semi-permeable membrane 138 in the form of a thin circular disc is located above the first spacer ring 136 such that the semi-permeable membrane 138 is spaced apart from the first circular porous filter 134 by the first spacer ring 136. A second spacer ring 140 of ABS material is located above the semi-permeable membrane 138 and a second porous filter 142 is located above the second spacer ring and helps to prevent dirt or debris from the aperture 130 from passing to the semi-permeable membrane 138 from the basin 104. The semi-permeable membrane 138 is also spaced apart from the second porous filter 142 by the second spacer ring 140. The spacer rings 136, 140 prevent contact of the semi-permeable membrane with the porous filters 134, 142 to prevent wicking of water through the semi-permeable membrane through contact with the porous filters 134, 142.

The peripheral edges of the thin-disk shaped first and second porous circular filters 134, 142 and of peripheral edges of the thin-disk shaped semi-permeable membrane 138 are fixed to respective surfaces of the spacer rings 136, 140 with an adhesive silicone sealant material.

In the present application, semi-permeable means that the material is not porous to allow water to freely flow through it. Rather, semi-permeable is intended to mean that water flows through the material but at a reduced rate. One type of material used for a semi-permeable membrane 138 according to the present invention is a sheet of tent fabric, that breathes while still being water resistant. The function of the semi-permeable membrane 138 is to provide a long time constant for controlled release of water from the water chamber 122. Keeping water in the water chamber prevent activation of a water source until after the time that the water level in the water chamber 122 has dropped below a predetermined level.

A switch assembly includes an elongated switch mounting bracket 144 that is positioned within the water chamber 122. An upper lateral extension of the bracket 144 is captured between the top of the tubular pipe 106 and the bottom of the basin 104. A lower lateral extension of the switch mounting bracket has an aperture 130 formed there through for receiving a threaded body of a magnetically actuated switch 150. The switch 150 includes an enlarged base 152 that stops against a lower face of the lower lateral extension 148. A nut 154 engages the threaded body of the switch 150 to fasten the switch to the bracket 144.

A hollow cylindrical float member 156 with a magnet embedded therein moves up and down along a downwardly extending longitudinal switch stem 154 between a proximate and a distal position with respect to the magnetically actuated switch module 148. An O-ring 160 engages a groove formed in the distal end of the switch stem 154 and serves a stop for the float member 156. In a lower distal position, the switch 156 is normally closed. In an upper proximate position, the magnet in the float member 156 actuates the switch 156 to keep it open. In operation, a high water level in the water chamber 122 keeps the magnetically actuated switch 156 in an open condition.

The length of the cylindrical tubular pipe 106 and the length of the elongated bracket 144 can be set to various lengths to predetermine the water level within the water chamber at which the switch is actuated, that is opened. The switch 156 is connected to a pair of wires 162 that extend up through the water chamber 122 and through a grommet 164 in the wall of the basin 104 to an external water control device, such as a water valve or a control circuit. The control signal actuates a water control valve or a control circuit to provide water from a source, some of which water is received and retained for a time in the water chamber 122. Using this system the water control valve is not open for water flow from a water source unless the water level in the water chamber 122 is below a predetermined level.

In use, this embodiment of the invention provides for a slow release of water from the water chamber 122 through the semi-permeable membrane 138, for example, over a one hour period. This prevents the possibility of overwatering due to water saturated soil. In the case where water leaks back up through the semi-permeable membrane 138 and into the water chamber 122 from below, a high water level (that is, a water level above the predetermined threshold) in the water chamber 122 prevents a water source from being actuated.

The foregoing descriptions of a specific embodiment of the present invention have been presented for purposes of illustration and description. It is not intended to be exhaustive or to limit the invention to the precise forms disclosed, and obviously many modifications and variations are possible in light of the above teaching. The embodiment was chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

The invention claimed is:

1. Soil moisture sensing apparatus, comprising:
   a housing embedded in the soil and having a water chamber that is adapted to receive water;
   means coupled to the lower end of said housing for controllably releasing water from said water chamber, wherein the means coupled to the lower end of said housing for controllably releasing water from said water chamber includes:
   a first porous filter;
   a first spacer ring located above the first filter;
   a semi-permeable membrane located above the first spacer ring;
   a second spacer ring located above the semi-permeable membrane;
   a second porous filter located above the second spacer ring; and
   wherein the first and second filters are spaced apart from the semi-permeable membrane; and
   water level sensing means for sensing a predetermined water level in said water chamber.

2. The apparatus of claim 1 wherein the water level sensing means for indicating a predetermined water level in said water chamber includes a water level sensor that is adapted to provide a control signal.

3. The apparatus of claim 2 wherein the water level sensor includes a float that actuates a switch that is adapted to provide the control signal.

4. The apparatus of claim 3 wherein the water level sensor includes a float that magnetically actuates the switch that is adapted to provide the control signal.

5. The apparatus of claim 1 wherein the water chamber comprises a hollow cylindrical tube that has a lower end to which is coupled to the means for controllably releasing water from said water chamber.

6. The apparatus of claim 5 wherein the lower end of the hollow cylindrical tube is coupled to the means for controllably releasing water from said water chamber and said means for controllably releasing water includes an end cap assembly that includes:

a cap having a base plate with an aperture formed therein and having a cylindrical peripheral flange, contained within the cap member are:

said first porous filter located adjacent the base plate;

said first spacer ring located above the first porous filter;

said semi-permeable membrane located above the first spacer ring;

said second spacer ring located above the semi-permeable membrane;

said second porous filter located above the second spacer ring.

7. The apparatus of claim 1 wherein the housing includes an upper basin that is coupled to the upper end of the chamber and that is adapted to receive water from a source.

8. The apparatus of claim 7 including a porous filter located within said upper basin.

9. The apparatus of claim 7 including a grate that covers said upper basin.

* * * * *